(12) United States Patent
Smith

(10) Patent No.: US 8,133,245 B2
(45) Date of Patent: Mar. 13, 2012

(54) SURGICAL APPARATUS WITH ANNULAR PENETRATOR

(75) Inventor: Robert C. Smith, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 189 days.

(21) Appl. No.: 12/526,052

(22) PCT Filed: Feb. 15, 2008

(86) PCT No.: PCT/US2008/002075
§ 371 (c)(1),
(2), (4) Date: Aug. 6, 2009

(87) PCT Pub. No.: WO2008/103308
PCT Pub. Date: Aug. 28, 2008

(65) Prior Publication Data
US 2010/0324486 A1   Dec. 23, 2010

Related U.S. Application Data

(60) Provisional application No. 60/902,417, filed on Feb. 20, 2007.

(51) Int. Cl.
*A61B 17/32* (2006.01)
(52) U.S. Cl. ......................................... 606/180; 606/170
(58) Field of Classification Search .................. 606/167, 606/170–172, 176, 178–180; 604/164.11, 604/164.12, 264, 506
See application file for complete search history.

(56) References Cited

U.S. PATENT DOCUMENTS

| 3,837,345 | A | * | 9/1974 | Matar | 606/159 |
| 5,372,588 | A | | 12/1994 | Farley et al. | |
| 5,556,411 | A | * | 9/1996 | Taoda et al. | 606/185 |
| 5,591,186 | A | * | 1/1997 | Wurster et al. | 606/170 |
| 5,690,664 | A | * | 11/1997 | Sauer et al. | 606/185 |
| 5,697,913 | A | * | 12/1997 | Sierocuk et al. | 604/164.11 |
| 5,860,996 | A | | 1/1999 | Urban et al. | |
| 6,077,284 | A | | 6/2000 | Piraka | |
| 6,270,501 | B1 | | 8/2001 | Freiberg et al. | |
| 6,296,651 | B1 | | 10/2001 | Lary et al. | |
| 6,497,714 | B1 | * | 12/2002 | Ishikawa et al. | 606/169 |

(Continued)

FOREIGN PATENT DOCUMENTS
WO  WO 0102123 A  3/2001
(Continued)

OTHER PUBLICATIONS

International Search Report for PCT/US2008/002075—date of mailing is May 20, 2008 (1 page).

*Primary Examiner* — Elizabeth Houston

(57) ABSTRACT

A surgical apparatus for penetrating tissue includes an outer member defining a longitudinal axis and having an outer peripheral wall and an inner member at least partially disposed within the outer member. The inner member includes a penetrating member adjacent the distal end of the outer member. The penetrating member has a substantially annular peripheral edge adapted to penetrate tissue. The inner member and the outer member are adapted for relative longitudinal movement between first and second longitudinal positions. In the first position, the annular peripheral edge of the penetrating member is substantially confined within the outer peripheral wall of the outer member and wherein, in the second position, the annular peripheral edge is at least partially exposed from the outer peripheral wall to facilitate penetration through tissue.

11 Claims, 6 Drawing Sheets

U.S. PATENT DOCUMENTS

| | | |
|---|---|---|
| 6,656,198 B2 * | 12/2003 | Tsonton et al. ............... 606/167 |
| 6,673,088 B1 * | 1/2004 | Vargas et al. ................. 606/185 |
| 6,837,874 B1 | 1/2005 | Popov |
| 7,258,694 B1 * | 8/2007 | Choi et al. .................... 606/184 |
| 2002/0143236 A1 | 10/2002 | Sauer et al. |
| 2007/0142852 A1 * | 6/2007 | Lee et al. ...................... 606/170 |
| 2009/0306697 A1 * | 12/2009 | Fischvogt .................... 606/185 |

FOREIGN PATENT DOCUMENTS

| | | |
|---|---|---|
| WO | WO 2007/035889 A | 3/2007 |

\* cited by examiner

SURGICAL APPARATUS WITH ANNULAR PENETRATOR

CROSS REFERENCE TO RELATED APPLICATIONS

This application is a National Stage Application of PCT/US2008/002075 filed Feb. 15, 2007 under 35 USC 371(a), which claims priority of U.S. Provisional Patent Application Ser. No. 60/902,417 filed Feb. 20, 2007 the entire contents of which are hereby incorporated by reference.

BACKGROUND

1. Technical Field

The present disclosure relates to a surgical apparatus for use in minimally invasive surgical procedures, such as endoscopic or laparoscopic type procedures.

2. Background of the Related Art

Minimally invasive procedures are continually increasing in number and variation. Forming a relatively small diameter temporary pathway to the surgical site is a key feature of most minimally invasive surgical procedures. The most common method of providing such a pathway is by inserting a trocar assembly through the skin. In many procedures, the trocar assembly is inserted into an insufflated body cavity of a patient. In such procedures, the trocar assemblies with seal mechanisms are utilized to provide the necessary pathway to the surgical site while minimizing leakage of insufflation gases.

Trocar assemblies typically include an obturator which is removably inserted through a cannula. The obturator may include a safety shield which protects against unintentional puncturing by the sharpened tip of the obturator. The safety shield includes a mechanism which controls the relative movement and locking of the safety shield. One example of a safety shield mechanism is disclosed in commonly assigned U.S. Pat. No. 6,319,266 to Stellon et al., the entire contents of which are hereby incorporated by reference.

Accordingly, the present disclosure is directed to further improvements in trocar assemblies.

SUMMARY

A surgical apparatus for penetrating tissue includes an outer member defining a longitudinal axis and having an outer peripheral wall and an inner member at least partially disposed within the outer member. The inner member includes a penetrating member adjacent the distal end of the outer member. The penetrating member has a substantially annular peripheral edge adapted to penetrate tissue. The inner member and the outer member are adapted for relative longitudinal movement between first and second longitudinal positions. In the first position, the annular peripheral edge of the penetrating member is substantially confined within the outer peripheral wall of the outer member and wherein, in the second position, the annular peripheral edge is at least partially exposed from the outer peripheral wall to facilitate penetration through tissue.

A housing member is mounted adjacent the proximal end of the outer member. The outer member may be adapted for longitudinal movement relative to the housing member and the inner member to move between the first and second longitudinal positions. The outer member may be biased toward the second longitudinal position.

The penetrating member may define a cross-sectional dimension inclusive of the peripheral edge generally approximating an outer dimension of the outer member. The penetrating member may be longitudinally spaced from the distal end of the outer member when in the second longitudinal position. The distal end of the outer surface may define an atraumatic nose and in one embodiment is substantially closed.

The outer member defines a longitudinal guide channel for at least partially receiving the inner member. The inner member traverses the guide channel upon longitudinal movement of the outer member between the first and second longitudinal positions. The outer member includes opposed slots extending through the outer wall. The annular peripheral edge extends through the opposed slots upon movement of the outer member to the second longitudinal position.

The inner member and the penetrating member may be monolithically formed.

The surgical apparatus also may include a cannula with the outer member and the inner member being positionable within the cannula.

BRIEF DESCRIPTION OF THE DRAWINGS

Preferred embodiments of the present disclosure are described hereinbelow with references to the drawings, wherein.

DETAIL DESCRIPTION OF PREFERRED EMBODIMENTS

Figure 1:
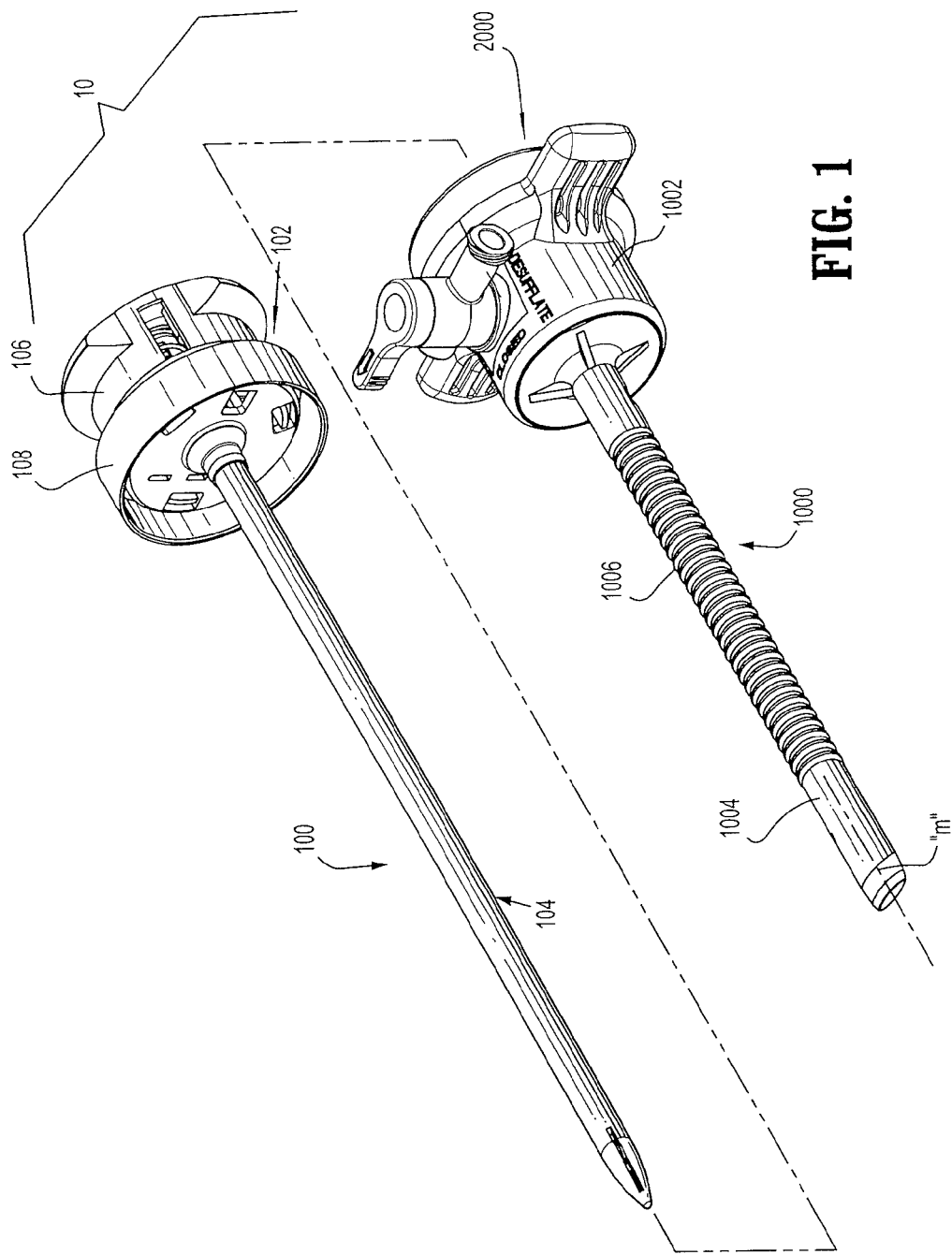
FIG. 1 is a perspective view of a surgical apparatus in accordance with the principles of the present disclosure illustrating the cannula and obturator which is positionable within the cannula.
Figure 2:
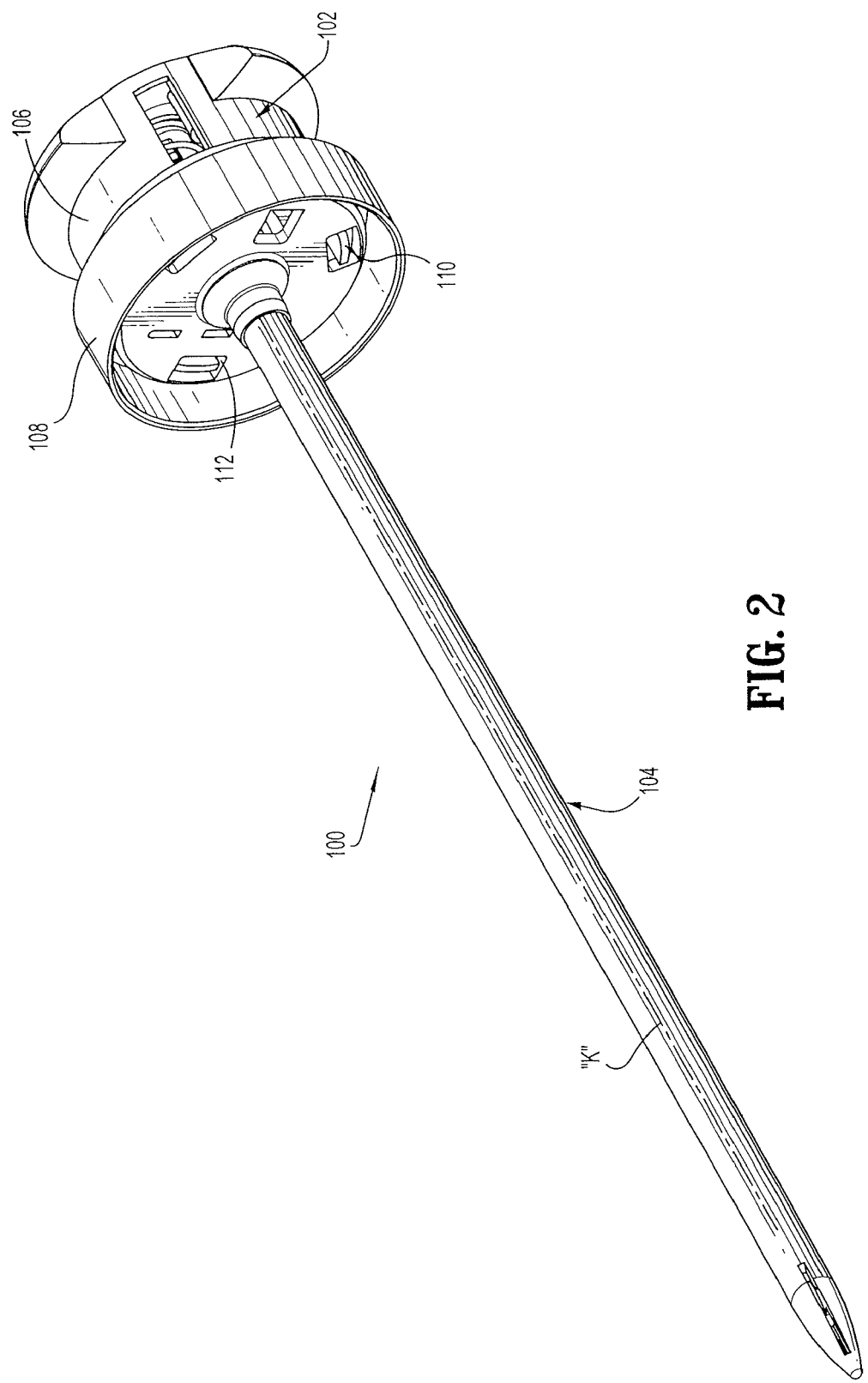
FIG. 2 is a perspective view of the obturator of the surgical apparatus of FIG. 1.

Referring now in detail to the drawing figures, in which, like references numerals identify similar or identical elements, there is illustrated, in FIGS. 1 and 2, a surgical apparatus constructed in accordance with a preferred embodiment of the present disclosure and designated generally by reference numeral 10. Surgical apparatus 10 is particularly adapted for use in minimally invasive surgical procedures such as endoscopic or laparoscopic procedures. Generally, surgical apparatus 10 includes two principal subassemblies, namely, obturator assembly 100 and cannula assembly 1000.

Cannula assembly 1000 may be any cannula assembly suitable for use in a laparoscopic surgical procedure. In one preferred embodiment, cannula assembly 1000 includes cannula housing 1002 and cannula sleeve 1004 extending from the cannula housing 1002. Either or both cannula housing 1002 and cannula sleeve 1004 may be transparent in part or in whole and may be fabricated from biocompatible metal or polymeric material. Cannula sleeve 1004 may include locking ribs 1006 on its external surface. Locking ribs 1006 are structured to engage tissue and assist in retention of cannula sleeve 1004 within the tissue to prevent retroplusion of the cannula sleeve 1004 from the tissue. Locking ribs 1006 may be spaced along longitudinal axis "m" of cannula sleeve 1004. Cannula assembly 1000 may include an internal seal such as a duck-bill valve or other zero closure valve adapted to close in the absence of a surgical instrument to prevent passage of insufflation gases through the cannula assembly 1000.

Surgical apparatus 10 may also include a seal assembly 2000 which is preferably releasably mounted to cannula housing 1002. Means for releasably connecting seal assembly 2000 to cannula housing 1002 may include a bayonet coupling, threaded connection, latch, friction fit, tongue and groove arrangements, snap-fit, or the like. Seal assembly 2000 includes seal housing 2002 and at least one internal seal which is adapted to form a fluid tight seal about an instrument inserted through the seal assembly 2000. One suitable seal may be the fabric seal disclosed in commonly assigned U.S. Pat. No. 6,702,787, which issued Mar. 9, 2003, the entire contents of which are incorporated herein by reference. The seal disclosed in the '787 patent may be a flat septum seal having a first layer of resilient material and a second fabric layer juxtaposed relative to the first layer. Further details of the seal may be ascertained by reference to the '787 patent. Seal assembly 2000 may or may not be a component of cannula assembly 1000. For example, the seal assembly may be a separate, removable assembly. In the alternative, the seal assembly may comprise an integral part of the cannula assembly 1000 and not be removable.

Figure 3:
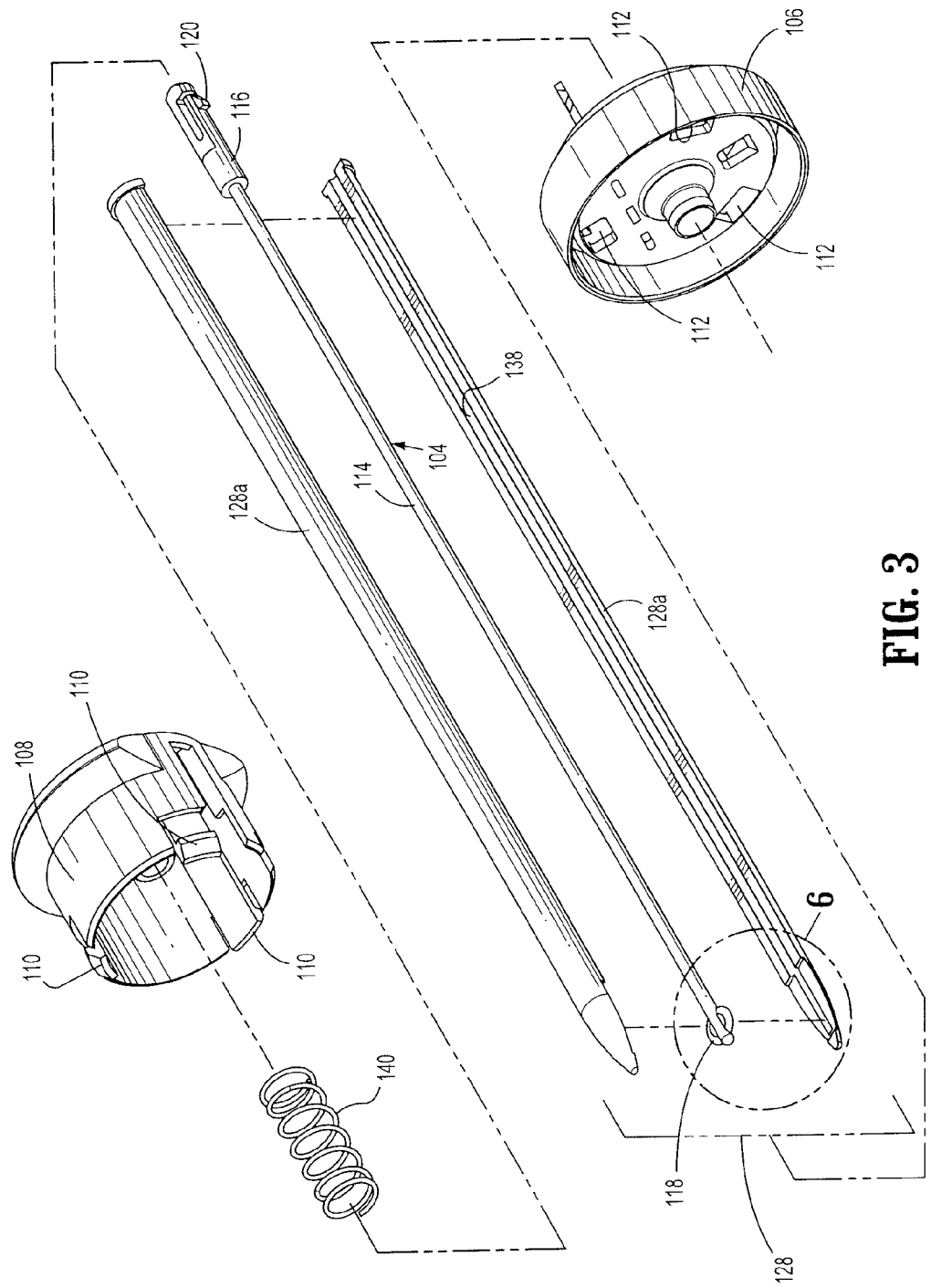
FIG. 3 is a perspective view with parts separated of the obturator illustrating the obturator housing, outer member and the inner member with the annular penetrating member thereto mounted.
Figure 7:
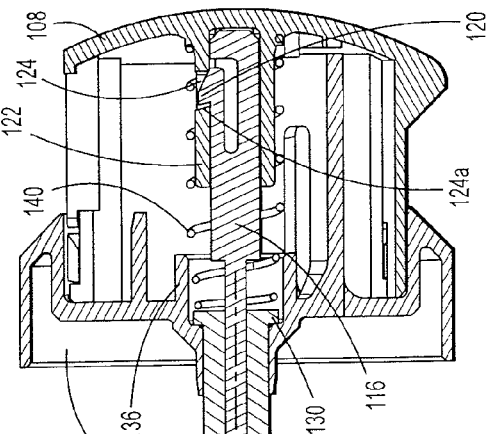
FIG. 7 is a plan view of the leading end portion of the obturator further illustrating the first longitudinal position of the outer member and the associated relationship of the inner member and the penetrating member.
Figure 4:
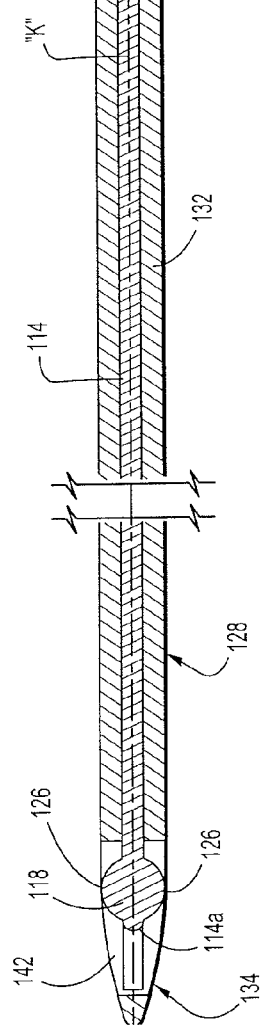
FIG. 4 is a side cross-sectional view of the obturator illustrating the outer member in a first longitudinal position relative to the inner member and the penetrating member.

With reference now to FIGS. 3-4, in conjunction with FIG. 2, obturator assembly 100 includes obturator housing 102 and obturator shaft or inner member 104 extending distally from the housing 102. Inner member 104 defines longitudinal axis "k" and will be discussed in greater detail hereinbelow. Obturator housing 102 includes housing base 106 and housing cover 108. Once the appropriate components are positioned therewithin (as described below), housing base 106 may be attached to housing cover 108 by engaging mating surfaces, for example, by resilient latches 110 of cover 108 interlocking with correspondingly dimensioned latch openings 112 of housing base 106. Preferably, to uniformly connect base 106 and cover 108 at least three corresponding latches 110 and openings 112 are spaced evenly around the circumference of the cover 108 and the base 108, respectively.

Inner member 104 includes inner rod 114, rod mount 116 adjacent the proximal end of the inner rod 114 and penetrating member 118 adjacent the distal end of the inner rod 114. Rod mount 116 secures inner member 104 within obturator housing 102 and longitudinally fixes the inner member 104 to the obturator housing 102. In one embodiment, rod mount 116 includes deflectable locking detent 120. As best depicted in FIG. 4, housing cover 108 of obturator housing 102 includes mounting extension 122 depending within the interior of the housing cover 108 in general alignment with the longitudinal axis "k". Mounting extension 122 defines locking slot 124 which receives locking detent 120 during insertion and assembly of rod mount 116 within mounting extension 122 of housing cover 108. During insertion, locking detent 120 will flex radially inwardly whereby upon encountering locking slot 124 will return under its inherent resiliency to engage locking shelf 124a adjacent locking slot 124 in secured relation.

Referring to FIGS. 4-7, penetrating member 118 is preferably annular in configuration and defines outer peripheral or circumferential edges 126 extending radially outwardly relative to inner rod 114. Peripheral edges 126 each extend through major arc portions of the circumference of penetrating member 118. In one embodiment, peripheral edges 126 are generally atraumatic to tissue to perform a dissecting or penetrating function with the tissue without incising or piercing the tissue. In an alternative, peripheral edges 126 may be sharpened to incise tissue. Penetrating member 118 is disclosed as generally round or wheel-like in configuration. Penetrating member 118 defines a reduced profile, e.g., is relatively thin, adjacent peripheral edges 126, which enhances passage through tissue. Other configurations are also envisioned including elliptical, oblong, polygonal or the like. In addition, penetrating member 118 is spaced a predetermined distance "b" (FIG. 7) from the distal end 114a of inner rod 114.

In one embodiment, inner member 104 including inner rod 114, rod mount 116 and penetrating member 118 are monolithically formed as a single unit. Suitable materials of construction of inner member 104 including biocompatible materials such as stainless steel, titanium, or a suitable polymeric material such as an acrylic, polycarbonate or the like manufactured under known injection molding techniques.

With continued reference to FIGS. 4-7, in conjunction with FIG. 1, obturator assembly 100 further includes protective shield or outer member 128 which is coaxially positioned about inner member 104. Outer member 128 is adapted for reciprocal longitudinal movement relative to obturator housing 108, inner member 104 and penetrating member 118. Outer member 128 includes proximal mounting collar 130, main outer body 132 and distal or leading guard 134. Outer member 128 may be monolithically formed as a single unit with any of the aforementioned biocompatible materials mentioned in connection with inner member 104. In one embodiment, outer member 128 includes longitudinal sections 128a. Longitudinal sections 128a may be secured to each other by conventional means subsequent to assembly of inner member 104 within outer member 128. Such means may include adhesives, glues, snap fits, or the like.

Mounting collar 130 of outer member 128 is received within cylindrical mount 136 of base 108 of obturator housing 102 to mount outer member 128 relative to the obturator housing 102. Mounting collar 130 may traverse cylindrical mount 136 during longitudinal movement of outer member 128 along inner rod 114 and relative to obturator housing 102. Outer member 128 defines longitudinal bore 138 for reception of inner rod 114 of inner member 104 in a manner whereby the outer member 128 may move in reciprocal longitudinal directions along the inner member 104 between a first relative advanced position depicted in FIG. 4 and a second relative retracted position as will be discussed.

Outer member 128 may be spring biased in the distal direction by coil spring 140. At its proximal or trailing end, coil spring 140 is positioned coaxially about mounting extension 122 and about the proximal end of inner member 104, and, at its distal end, is received within cylindrical mount 136 in engagement with mounting collar 130 of outer member 128. In this manner, coil spring 140 normally biases outer member 128 in the distal direction.

Figure 6:
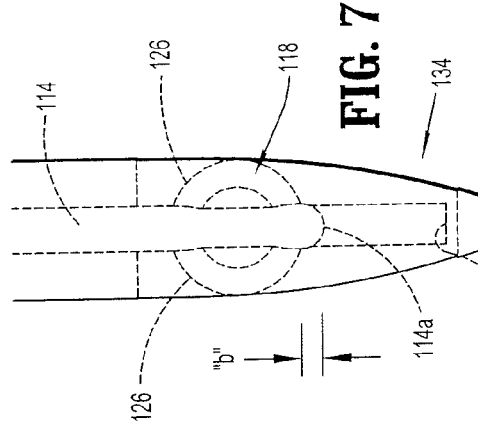
FIG. 6 is an enlarged isolated view of the area of detail identified in FIG. 3 illustrating a mounting arrangement of the annular penetrating member and the outer member.
Figure 5:
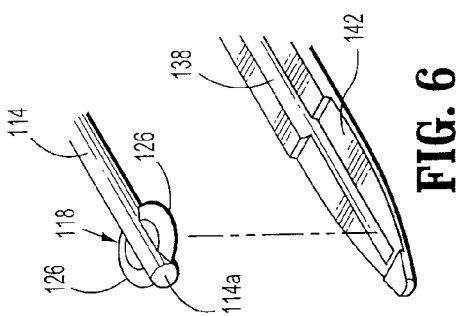
FIG. 5 is a perspective view of the leading end portion of the obturator illustrating the annular penetrating member confined within the outer member when in the first longitudinal position of the outer member.

Referring now to FIGS. 4-6, leading guard 134 of outer member 128 is generally tapered, and may incorporate an ogive or frusto-conical configuration as shown. The interior of leading guard 134 includes internal recess 142 adapted to accommodate penetrating member 118 and arranged to permit the leading guard 134 to move along the penetrating member 118 during longitudinal movement of outer member 128. Leading guard 134 further defines diametrical openings or slots 144 within the wall of leading guard 134 in communication with internal recess 142. Penetrating member 118 at least partially extends through openings 144 when in the second retracted longitudinal position of outer member 128. Leading guard 134 defines arcuate distal nose 146 which is arranged to penetrate or pass through tissue in an atraumatic manner. Distal nose 146 is closed, i.e., devoid of any openings or voids, which would otherwise undesirably receive tissue during penetration and detract from the penetrating capabilities of obturator assembly 100.

Figure 8:
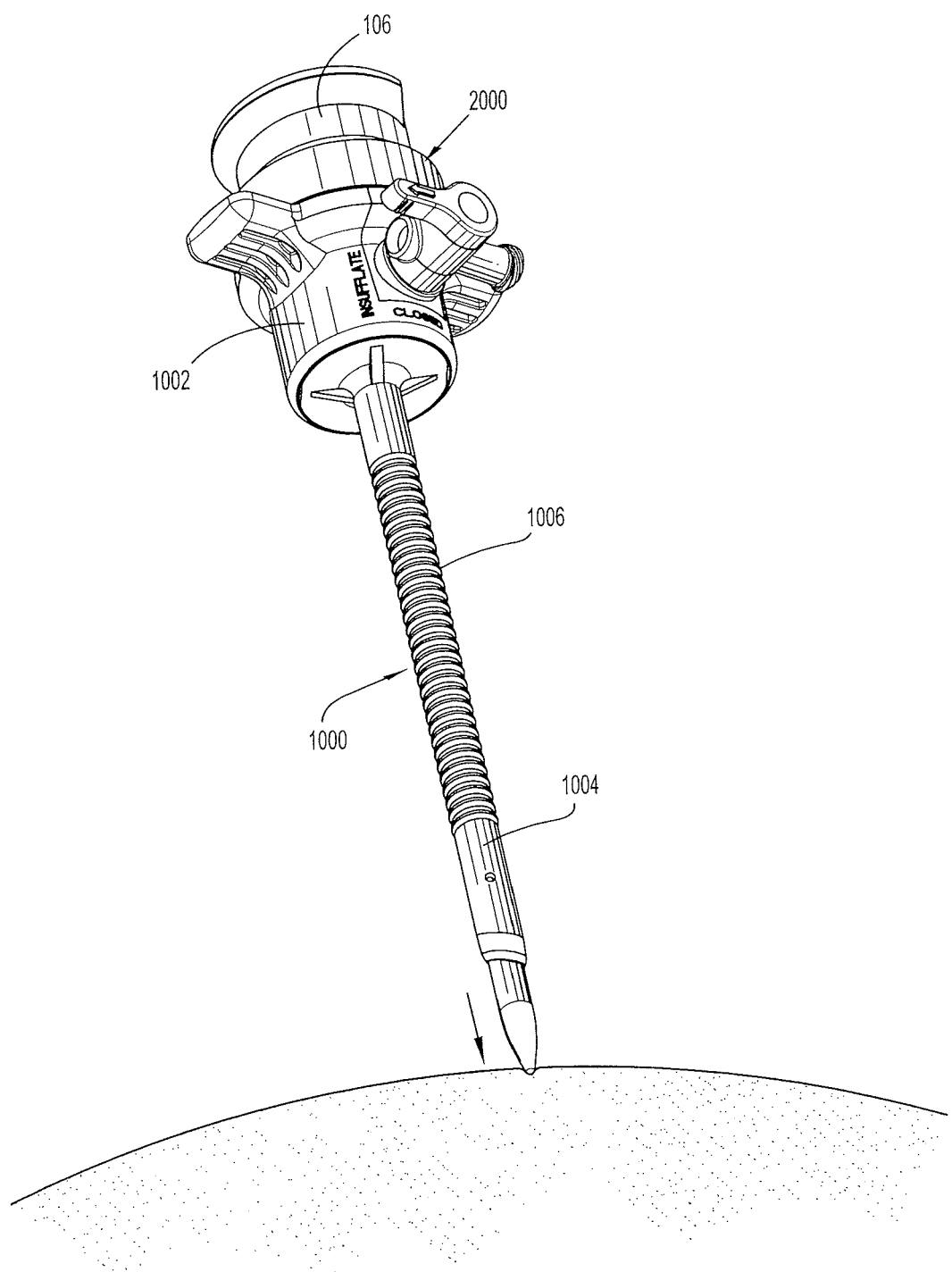
FIG. 8 is a view illustrating the surgical apparatus applied against body tissue.
Figures 9, 10:
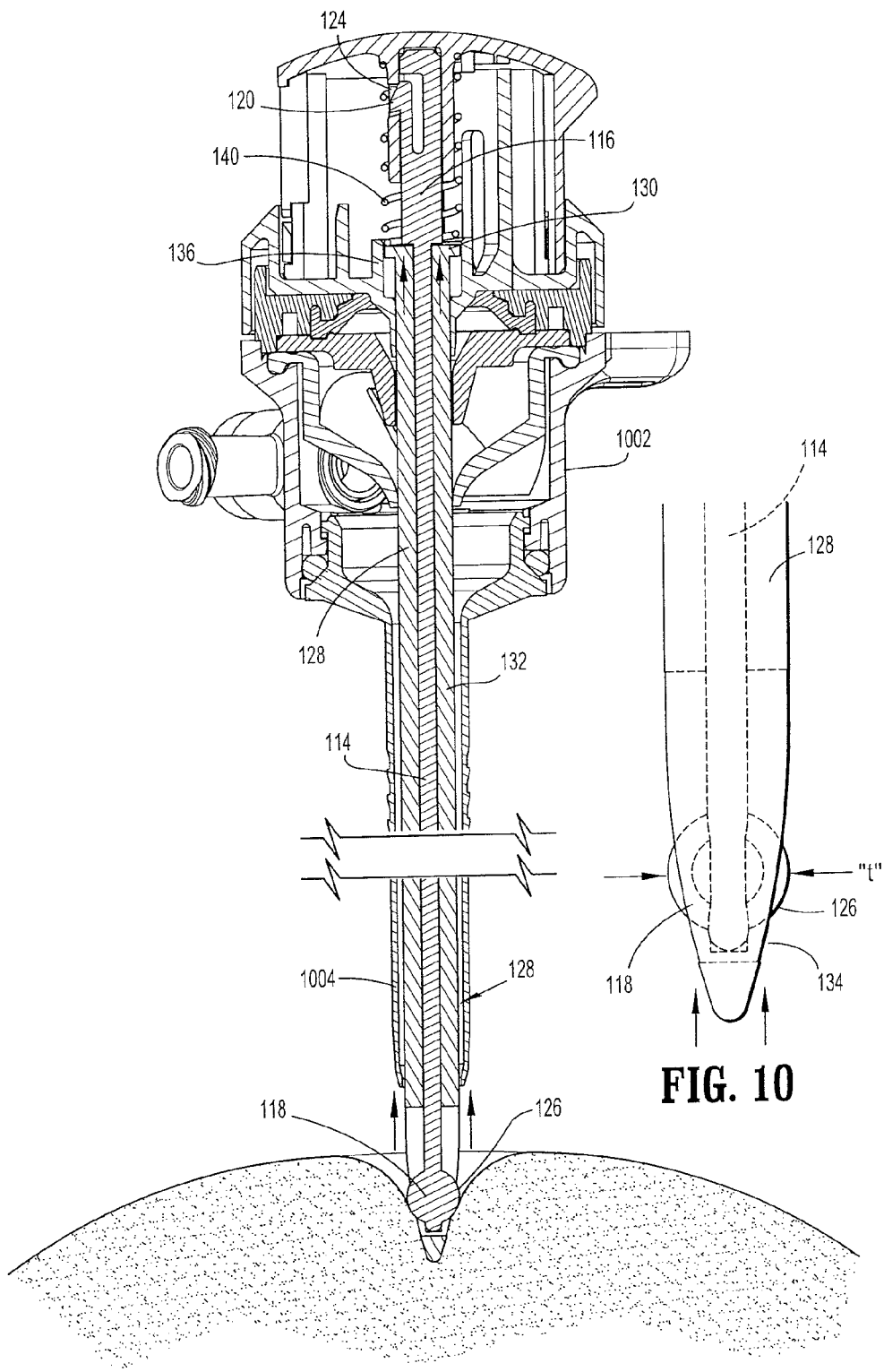
FIG. 9 is a view illustrating the surgical apparatus in cross-section and movement of the outer member to the second longitudinal position relative to the inner member and the penetrating member upon engagement of the outer member with the tissue.
FIG. 10 is a plan view of the leading end portion of the obturator similar to the view of FIG. 7 illustrating the outer member in the second longitudinal position with the penetrating member at least partially exposed.

The use of the surgical apparatus will now be discussed. Referring now to FIG. 8, the surgeon begins to insert the assembled surgical apparatus 10 through the body wall, e.g., insufflated abdominal cavity, of the patient. Leading guard 134, specifically, initially distal nose 146, contacts the tissue and, through the counterforce applied by the tissue, outer member 128 is driven upwardly against the bias of coil spring 140 from the first longitudinal position relative to inner member 104 depicted in FIGS. 4 and 7 to the second longitudinal position of FIGS. 9 and 10. This retracting movement exposes penetrating member 118 from leading guard 134 by virtue of the at least partial extension of peripheral edges 126 of the penetrating member 118 through opposed openings 144 of the leading guard 134. In the second longitudinal position, the distal end 114a of inner rod 114 contacts or "bottoms out" against end surface 138a of longitudinal bore 138 of outer member 128. With penetrating member 118 exposed, the surgeon may apply a distally-directed force to surgical apparatus 10 to cause penetration through the tissue. In particular, distal nose 146 of leading guard 134, in combination with the penetrating capabilities of peripheral edges 126 of penetrating member 118, facilitates passage through tissue in an atraumatic manner. In one embodiment, the cross-sectional dimension or diameter "t" of penetrating member 118 inclusive of peripheral edges 126 may approximate the outer diameter of main body 132 of outer member 128 (see FIG. 10). Thus, once peripheral edges 126 pass through tissue, outer member 128 and cannula sleeve 1004 may readily continue through the tissue with minimal effort by the surgeon.

Upon passage of penetrating member 118 and leading guard 134 through the body wall of the patient, leading guard 134 is no longer constrained and is free to move in a distal direction relative to penetrating member 118. Consequently, outer member 128 is driven distally under the influence of coil spring 140 to the first relative longitudinal position of FIG. 1 with leading guard 134 confining penetrating member 118. Obturator assembly 100 is removed from cannula assembly 1000 and surgery is performed with instruments inserted through cannula assembly 1000.

Except where noted otherwise, the materials utilized in the components of the presently disclosed trocar assembly generally include materials such as, for example, ABS, polycarbonate, stainless steel, titanium and any other suitable biocompatible metals and/or polymeric materials. A preferred ABS material is CYCOLAC which is available from General Electric. A preferred polycarbonate material is also available from General Electric under the trademark LEXAN. An alternative polycarbonate material which may be utilized is CALIBRE polycarbonate available from Dow Chemical Company. The polycarbonate materials may be partially glass filled for added strength.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A surgical apparatus for penetrating tissue, which comprises:
an outer member defining a longitudinal axis and having proximal and distal ends, the outer member having an outer peripheral wall and a longitudinal guide channel including a distal end surface;
an inner member at least partially disposed within the longitudinal guide channel of the outer member, the inner member including a penetrating member positioned proximally adjacent to and spaced-apart from the distal end of the inner member, the penetrating member having a substantially annular peripheral edge adapted to penetrate tissue, the inner member configured to traverse the guide channel upon longitudinal movement of the outer member relative to the inner member between first and second longitudinal positions, wherein, in the first position, the distal end of the inner member is spaced-apart from the distal end surface of the guide channel of the outer member such that the annular peripheral edge of the penetrating member is substantially confined within the outer peripheral wall of the outer member, and, wherein, in the second position, the distal end of the inner member traverses the guide channel to contact the distal end surface of the guide channel such that the annular peripheral edge of the penetrating member is at least partially exposed from the outer peripheral wall of the outer member to facilitate penetration through tissue.

2. The surgical apparatus according to claim 1 including a housing member mounted adjacent the proximal end of the outer member.

3. The surgical apparatus according to claim 2 wherein the outer member is adapted for longitudinal movement relative to the housing member and the inner member to move between the first and second longitudinal positions.

4. The surgical apparatus according to claim 3 wherein the outer member is biased toward the second longitudinal position.

5. The surgical apparatus according to claim 1 wherein the distal end of the outer surface defines an atraumatic nose.

6. The surgical apparatus according to claim 5 wherein the atraumatic nose is substantially closed.

7. The surgical apparatus according to claim 1 including a cannula, the outer member and the inner member positionable within the cannula.

8. The surgical apparatus according to claim 1, wherein the penetrating member defines a cross-sectional dimension inclusive of the peripheral edge generally approximating an outer dimension of a main outer body the outer member.

9. The surgical apparatus according to claim 1 wherein the penetrating member is longitudinally spaced from the distal end of the outer member when in the second longitudinal position.

10. The surgical apparatus according to claim 1 wherein the outer member includes opposed slots extending through the outer wall, the annular peripheral edge extending through the opposed slots upon movement of the outer member to the second longitudinal position.

11. The surgical apparatus according to claim 1 wherein the inner member and the penetrating member are monolithically formed.

* * * * *